United States Patent [19]

Thomann

[11] 4,178,800
[45] Dec. 18, 1979

[54] METHOD OF AND APPARATUS FOR THE MEASURING OF QUANTITIES OF HEAT

[76] Inventor: Christoph Thomann, Pfannenstielstrasse 7, CH-8132 Egg, Switzerland

[21] Appl. No.: 908,371

[22] Filed: May 22, 1978

Related U.S. Application Data

[63] Continuation-in-part of Ser. No. 819,058, Jul. 26, 1977, abandoned.

[30] Foreign Application Priority Data

Sep. 22, 1976 [CH] Switzerland .................. 11988/76

[51] Int. Cl.² ........................................... G01K 17/00
[52] U.S. Cl. ................................................. 73/190 R
[58] Field of Search ....................... 73/15 B, 190 R

[56] References Cited

U.S. PATENT DOCUMENTS

| | | | |
|---|---|---|---|
| 2,982,132 | 5/1971 | Mendlowitz | 73/190 |
| 3,379,061 | 4/1968 | Mercier | 73/190 |
| 3,508,056 | 4/1970 | Fricke | 73/190 |
| 3,813,937 | 6/1974 | Fletcher et al. | 73/190 |
| 3,869,914 | 3/1975 | Koehler et al. | 73/190 |
| 3,942,378 | 3/1976 | Olmstead | 73/20 X |

OTHER PUBLICATIONS

Andersen, "Polymerization Rates by Calorimetry", in Journal of Polymerscience A-1, vol. 7, 1979, pp. 2889-2896.

*Primary Examiner*—Herbert Goldstein
*Attorney, Agent, or Firm*—Craig and Antonelli

[57] ABSTRACT

A method and apparatus for measuring an unknown quantity of heat in a measuring zone formed by a vessel of good thermal conducting properties is carried out in such a manner that the measuring zone is supplied with a known quantity of heat and the quantity of heat of the measuring zone is given off to a cold zone, that the temperature of the measuring zone is always kept equal to the temperature of the environment and at the same time the dissipation of heat is kept constant by keeping the difference between the temperature of the measuring zone and the temperature of the cold zone always the same, and that the known quantity of heat supplied to the measuring zone is measured at a point outside of the vessel when the unknown quantity of heat is absent and when it is present, the difference between the known quantity of heat in the absence of the unknown quantity of heat on the one hand and the known quantity of heat in the presence of the unknown quantity of heat on the other hand being the measurement result for the unknown quantity of heat. The vessel includes a known heat source and a cold source is provided which is connected with the vessel by way of a heat-conducting element.

8 Claims, 3 Drawing Figures

METHOD OF AND APPARATUS FOR THE MEASURING OF QUANTITIES OF HEAT

This application is a continuation-in-part application of Ser. No. 819,058 filed July 26, 1977, entitled "Calorimeter" now abandoned.

BACKGROUND AND SUMMARY OF THE INVENTION

The invention relates to a method and an apparatus for measuring an unknown quantity of heat in a measuring zone.

So-called differential calorimeters are known to be calorimeters of high measuring precision. They comprise two completely similar vessels which contain measuring zones which have the same heat losses. While the unknown quantity of heat to be measured is supplied to one vessel, the second vessel is heated electrically by introducing a known measurable quantity of heat in such a manner that no temperature differences can be detected between the two vessels. Under these conditions, the two quantities of heat supplied are then identical. It is also possible to heat with a known quantity of heat only a single vessel which contains a single measuring zone, to ascertain the heat loss of the vessel, and then to carry out measurement with the unknown quantity of heat.

With both methods, there is a lack of precision in the measuring operations as a result of heat exchange with the environment and the like.

The invention has as its object to overcome this disadvantage. For this purpose a method for measuring an unknown quantity of heat in a measuring zone is carried out in such a manner according to the invention that the measuring zone is supplied with a known quantity of heat and the quantity of heat of the measuring zone is given off to a cold zone, that the temperature of the measuring zone is always kept equal to the temperature of the environment and at the same time the dissipation of heat is kept constant by keeping the difference between the temperature of the measuring zone and the temperature of the cold zone always the same, and that the known quantity of heat supplied to the measuring zone is measured when the unknown quantity of heat is absent and when it is present, the difference between the known quantity of heat in the absence of the unknown quantity of heat on the one hand and the known quantity of heat in the presence of the unknown quantity of heat on the other hand being the measurement result for the unknown quantity of heat.

An apparatus for carrying out this method with a vessel heat-insulated relative to the environment for receiving an unknown heat source is characterized according to the invention in that the vessel comprises a known heat source, that a cold source is provided which is connected with the vessel by way of a heat-conducting element, that heat sensors are provided one for each of the environments, the vessel and the cold source, and that an electrical control device is provided which controls the known heat source and the cold source through the agency of the heat sensors in such a manner that the temperature of the vessel is always equal to the temperature of the environment and at the same time the difference between the temperature of the vessel and the temperature of the cold source is always the same.

According to one particular constructional form of the apparatus, the cold source comprises an additional heat source which is so controlled by the control device that the difference between the temperature of the environment and the temperature of the cold source is always the same.

According to one particular constructional form of the apparatus, the known heat source is a transistor since to reach the possible accuracy of the calorimeter, the heat supplied to the vessel by the heater has to be measured with the same accuracy. With a transistor used as a linear heater in the present invention, the collector current (or the collector-emitter voltage) is exactly proportional to the heat production, if the collector-emitter voltage (or the collector current) is kept constant. Therefore, the electronical integration of the power yielding the total heat supplied the vessel within a given time can be performed easily with a high degree of accuracy. Also, the use of a squaring device, which has to be used in prior art arrangements such as in U.S. Pat. Nos. 3,813,937 and 2,982,132, and which limit the accuracy, can be avoided.

According to a further special constructional form of the apparatus, the cold source consists of Peltier elements.

The drawings show a constructional example of an apparatus for carrying out the method according to the present invention in simplified form, by means of which the method according to the invention will also be explained.

These and further objects, features and advantages of the present invention will become more obvious from the following description when taken in connection with the accompanying drawings which show, for purposes of illustration only, several embodiments in accordance with the present invention.

DETAILED DESCRIPTION OF THE PREFERRED EMBODIMENTS

Figure 1:
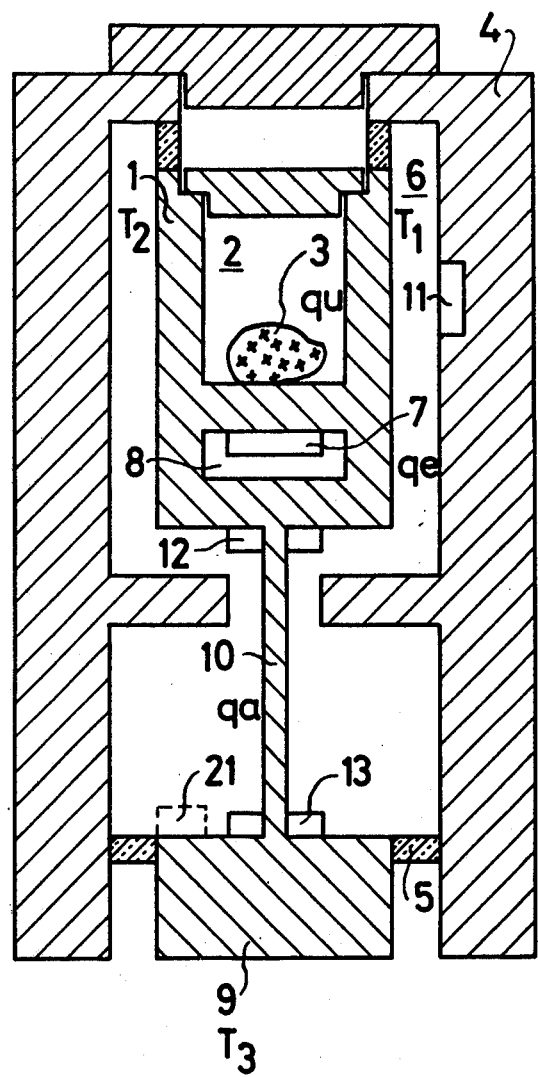
FIG. 1 shows a section through a calorimeter according to the present invention.

The calorimeter in FIG. 1 comprises a vessel 1 which contains the measuring zone 2 and is intended for receiving an unknown heat source 3. The wall of the vessel 1 is made of a material of good conducting properties, for example, copper. The vessel 1 is arranged in a massive housing 4 of a material which is good conductor, preferably a metal. This constructional form is useful for passive thermal stabilization. It is also possible to provide an active thermal stabilization. By means of insulation 5, a space 6 is provided between the vessel 1 and the housing 4, which contains insulation. In the illustrated constructional example, a heat-insulating vacuum is used, but it would also be possible to arrange a heat-insulating substance in the space 6.

The vessel 1 comprises a known electrical heat source 7. It is not important to the invention whether this heat source, as in the illustrated constructional example, is situated in a separate chamber 8 of the vessel 1 or in the interior of the vessel or at the outer side of the vessel. The electrical heat source 7 is referred to as known since the electrical energy supplying it can be measured precisely without any difficulty at any time.

One suitable heat source for use as the known heat source is a darlington transistor (which in actuality is a combination of two transistors). While darlington transistors are known per se (see The Semiconductor Data Library, 2nd Edition, published by Motorola Semiconductor Products, Inc.) for use in such applications as switching regulators, deflection circuits, invertors and chopper regulators, ignition circuits and high voltage switching power supplies, the application of such for use as a heat source for calorimetry apparatus has heretofore been unknown, applicant having discovered that the amount of heat generated by such a transistor arrangement, while small, is sufficient for calorimetry purposes and the precise degree to which it can be measured via the electrical energy supplied makes it an excellent reference heat source.

When the known heat source 7 is a transistor of which the collector-emitter voltage is kept constant, a collector current which is proportional to the heat supplied the vessel is provided with a high degree of accuracy. The linear relation between heat production and collector current permits the full utilization of the accuracy of the present invention. A transistor as a linear heating element is described in U.S. Pat. No. 3,942,378 for fluid flow measurements, but not for calorimetric applications.

Alternately, in a modified arrangement, the collector current of the transistor is kept constant, providing a collector-emitter voltage which is proportional to the heat supplied the vessel within a high degree of accuracy. This arrangement is significant because, in high precision applications, an important cause of error is the heat production of the wires connecting the known heat source in the vessel 7 with the control unit. By keeping the collector current constant, the heat production of the connecting wires remains also constant and, therefore, this heat production can be neglected with a neglegible resultant error.

Arranged below the vessel 1 as a cold source 9 is a Peltier cooling block. This cold source is connected to the vessel 1 by means of a strip of metal acting as a heat-conducting element 10.

The housing 4 comprises a heat sensor 11, the vessel 1, a heat sensor 12, the contacting element 10, the cold source 8, and a heat sensor 13. The heat sensor 11 measures the temperature $T_1$ of the environment of the vessel 1, at one end of heat conducting element 10 the heat sensor 12, the temperature $T_2$ of the vessel 1, and the heat sensor 13 the temperature $T_3$ of the cold source 9 at the other end of heat conducting element 10.

Figure 2:
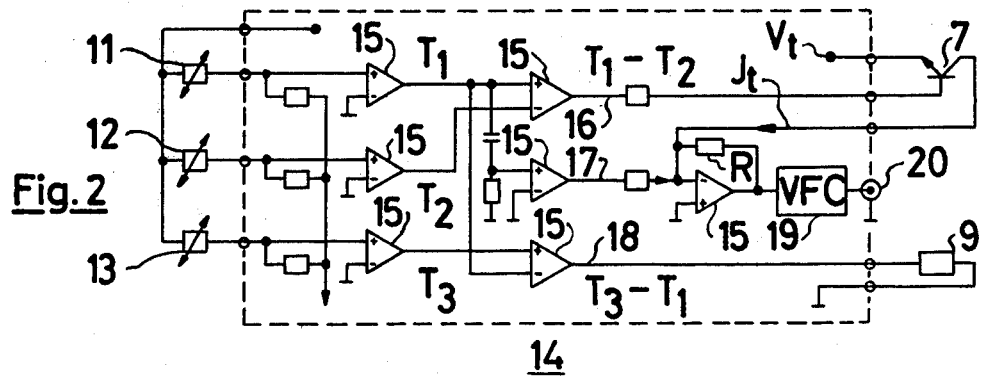
FIG. 2 shows a block diagram of an electrical control device for controlling the calorimeter according to FIG. 1, those elements of the calorimeter which are connected with the control device being shown in diagrammatic manner and provided with the same reference numerals.

As FIG. 2 shows, the known electrical heat source 7, the cold source 9 and the heat sensors 11, 12, 13 are connected to an electrical control device 14. The connection arrangement of the control device 14 is not important to the invention and will be readily understood by any person skilled in the art. In the case wherein a transistor type heat source is used the device 14 may comprise a total of seven amplifiers 15. The voltage at 16 gives the value $T_1$ minus $T_2$. The voltage at 17 compensates electronically for temperature variations in the environment. The voltage at 18 gives the value $T_3$ minus $T_1$. The electrical power which is supplied to the heat source 7 is $V_t \cdot J_t$. The transistor voltage $V_t$ is kept constant. The transistor current $J_t$ is converted by way of a resistance R into a voltage which is converted by a converter 19 into a frequency. This frequency is used at 20 for digital indications.

Figure 3:
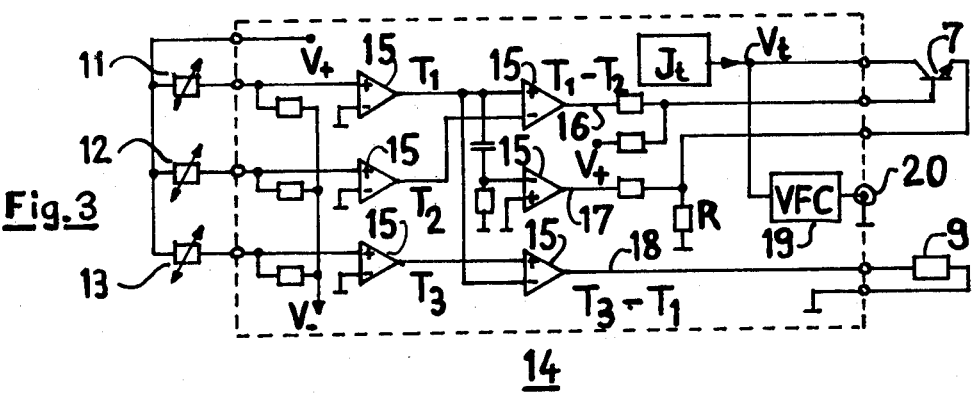
FIG. 3 is a block diagram similar to that of FIG. 2, but illustrating a modified arrangement.

The necessary modifications in the electrical control device for keeping the collector current constant instead of the collector-emitter voltage is shown in FIG. 3. In this arrangement, the constant voltage source $V_t$ is replaced by a constant current source $J_t$ and the converter 19 is connected directly to this point, while amplifier 15 is omitted and the resistor R is connected to ground.

The device operates as follows:

The heat present in the vessel 1 is dissipated by means of the heat-conducting element 10 towards the cold source 9. The known heat source 7 and the cold source 9 are controlled in such a manner by the control device 14 through the agency of the heat sensors 11, 12, 13 that the temperature $T_2$ of the vessel 1 is always identical to the temperature $T_1$ of the environment, and that at the same time the quantity $q_a$ of the heat dissipated by means of the heat conducting element 10 is kept constant by the fact that the difference between the temperature $T_2$ of the vessel and the temperature $T_3$ of the cold source 9 is always the same. Thus the sum of the known heat quantity $q_e$ of the known heat source 7 and the unknown heat quantity $q_u$ of the unknown heat source 3 is equal to the quantity of the dissipated heat quantity $q_a$; $q_a = q_e + q_u$.

Then without the unknown heat quantity $q_u$ of the unknown heat source 3, the known electrical heat quantity $q_{eNull}$ which is then required of the known electrical heat source 7 is just equal to the quantity of heat $q_a$ dissipated by way of the element 10 from the vessel 1 to the cold source 9. Thus, the unknown heat quantity $q_u$ is equal to the known electrical heat quantity $q_{eNull}$ in the absence of the unknown heat quantity $q_u$ minus the known electrical heat quantity $q_e$ in the presence of the unknown heat quantity $q_u$; $q_u = q_{eNull} - q_e$.

Thus, when with the described apparatus the known heat quantity $q_{eNull}$ in the absence of the unknown heat quantity 3 and then the known heat quantity $q_e$ in the presence of the unknown heat quantity 3 is measured, the difference between the two measured heat quantities of the known heat source 7 is the measurement result for the quantity of heat of the unknown heat source 3.

The advantages of the illustrated double-compensated calorimeter are as follows. Since the unknown heat quantity $q_u$ is compensated by the dissipation of heat $q_a$, the difference between the temperature $T_2$ of the vessel 1 and the temperature $T_1$ of the environment can be kept small. Thus, errors due to heat exchange with the environment are also small. The heat dissipation $q_a$ is constant, but kept greater than the quantity of heat $q_u$, and the surplus $q_a - q_u$ is compensated by the quantity of heat $q_e$ of the known heat source 7. As a result, it is not necessary to carry out the difficult business of absolute measurement of the dissipated heat quantity $q_a$, and also constant heat currents between the vessel 1 and the environment may be disregarded.

It is important to note that the detailed temperature distribution within the vessel is always a little bit different in the situation when the heat is supplied by the heat source than it is in the situation when the heat is supplied by the heater. Therefore, the heat flow may also change even though the temperature at the point of a heat sensor in the vessel remains constant, and this is a significant cause of error for the usual isothermal calorimeters. This disadvantage is avoided in the present invention by placing the heat sensor 12 outside of the vessel so that the heat flow in the thermal conductor 10 can be kept constant within a high degree of accuracy and independent of the actual thermal situation in the vessel. A similar circumstance applies to the situation in the heat sink, and as such, its heat sensor 13 is placed outside of the heat sink formed by the cold source 9. As a result, the temperature of the heat source 7 inside the vessel 1 does not have to be constant and even controlled variations of this temperature are permissible, thereby enlarging the applicable fields of the invention in relation to those of the usual isothermal calorimeters. Because the walls of the vessel are made of a material of good heat conducting properties, the temperature variations remain small on the outer surface of the vessel which is important in preventing heat exchange with the surroundings.

By using an electrical heat source as a known heat source, the absolute measurement of the heat quantity $q_u$ of the unknown heat source 7 can be carried out in a relatively simple and very precise manner, since the unknown heat quantity $q_u$ is directed equal to the difference between the known heat quantity $q_{eNull}$ in the absence of the unknown heat source 3 and the known heat quantity $q_e$ when the unknown heat source is present.

In this way, both exothermic and endothermic processes can be measured. With the illustrated double-compensated calorimeter, in test experiments, a precision of better than 0.1% and a resolution of 30 $\mu$W were achieved without any problem.

For more rapid stabilization of the cold source 9, it may be advantageous to add to the said source an additional heat source 21 which is also to be controlled by the control device 14, this being shown in dotted lines in FIG. 1.

In the illustrated constructional example, the unknown heat source 3 is a physical body. But, of course, the unknown heat source may also consist of radiation or other compositions.

While I have shown and described several embodiments in accordance with the present invention, it is understood that the same is not limited thereto, but is susceptible of numerous changes and modifications as known to those skilled in the art and I therefore do not wish to be limited to the details shown and described herein, but intend to cover all such changes and modifications as are encompassed by the scope of the appended claims.

I claim:

1. An apparatus for measuring an unknown heat quantity comprising: a vessel formed of a material having good heat conducting properties and heat-insulated relative to the environment and intended for receiving an unknown heat source, a known heat source associated with said vessel, a cold source connected with the vessel by way of a heat-conducting element, a first heat sensor located outside of said vessel for measuring a temperature $T_2$ of the vessel adjacent a connection between said vessel and said heat-conducting element, and a second heat sensor located outside of the cold source for measuring a temperature $T_3$ of the cold source adjacent a connection between said heat-conducting element and said cold source, a third heat sensor for measuring the temperature of the environment and an electrical control device for controlling the known heat source and the cold source by way of the heat sensors in such a manner that the temperature of the vessel is maintained equal to a temperature $T_1$ of the environment of the vessel in response to the difference sensed between the temperatures $T_1$ and $T_2$ and at the same time the difference between the temperature of the vessel and the temperature of the cold source is maintained the same in response to the difference sensed between $T_3$ and $T_1$.

2. An apparatus according to claim 1, characterized in that the cold source comprises an additional heat source which is additionally controlled by the control device in such a manner that the difference between the temperature of the vessel and the temperature of the cold source is always the same in response to the difference sensed between $T_3$ and $T_1$.

3. An apparatus according to claim 1, characterized in that the known heat source is a transistor.

4. An apparatus according to claim 1, characterized in that the cold source consists of Peltier elements.

5. An apparatus according to claim 3, wherein the control device comprises means for keeping the collector current of said transistor constant for providing a collector-emitter voltage proportional to heat supplied to the vessel.

6. An apparatus according to claim 3, wherein the control device comprises means for keeping the collector-emitter voltage constant for providing a collector current which is proportional to the heat suppled to the vessel.

7. A method of measuring an unknown heat quantity in a measuring zone formed by a vessel of good thermal conducting properties which is heat-insulated relative to the environment characterized in that a known quantity of heat is supplied to the measuring zone and the quantity of heat of the measuring zone is dissipated towards a cold source by way of a heat-conducting element connected at opposite ends to said vessel and cold source, respectively, that a vessel temperature $T_2$ is measured outside the vessel in the vicinity of the connection between the heat-conducting element and the vessel and that a cold source temperature $T_3$ is measured outside the cold source in the vicinity of the connection between the heat-conducting element and the cold source, that the heat dissipation is kept constant by arranging that the difference between the temperature $T_2$ and the temperature $T_3$ are maintained constant in response to the difference measured between $T_3$ and environment temperature $T_1$, that the temperature $T_2$ is kept at the same temperature as the environment temperature $T_1$ by controlling the temperature $T_2$ in response to the difference measured between the temperature $T_2$ and the temperature $T_1$, and that the known heat quantity supplied to the measuring zone is measured at a point outside of the vessel when the unknown quantity of heat is absent and present, the difference between the known quantity of heat when the unknown quantity of heat is absent and the known quantity of heat when the unknown quantity of heat is present being the measurement result for the unknown quantity of heat.

8. A method according to claim 7, comprising the step of controlling the temperature of the cold source in such a manner as to maintain the difference between the temperature of the vessel and the temperature of the cold source constant in response to the difference measured between $T_3$ and $T_1$.

* * * * *